United States Patent [19]

Sperti et al.

[11] Patent Number: 4,477,361

[45] Date of Patent: Oct. 16, 1984

[54] ANTIFUNGAL-ANTIBACTERIAL DETERGENTS CONTAINING CINNAMIC COMPOUNDS

[75] Inventors: George S. Sperti; Boris Sway, both of Cincinnati, Ohio

[73] Assignee: Sperti Drug Products, Inc., Erlanger, Ky.

[21] Appl. No.: 468,346

[22] Filed: Feb. 22, 1983

[51] Int. Cl.$^3$ .......................... C11D 9/50; C11D 3/48
[52] U.S. Cl. .................................... 252/106; 252/107
[58] Field of Search ............... 252/106, 107, 108, 122, 252/132, 89.1; 424/195, 365

[56] References Cited

U.S. PATENT DOCUMENTS

| | | | |
|---|---|---|---|
| 2,196,763 | 4/1940 | Figg | 252/107 |
| 3,043,778 | 7/1962 | Kelly | 252/107 |
| 3,355,392 | 11/1967 | Cantor et al. | 252/99 |
| 3,532,636 | 10/1970 | Pacini | 252/132 X |
| 3,598,746 | 8/1971 | Kaniecki et al. | 252/122 |
| 4,110,430 | 8/1978 | Hopp et al. | 424/65 |

FOREIGN PATENT DOCUMENTS 1281914 12/1961 France .

OTHER PUBLICATIONS

Balsam, M. S., et al., "Preservation of Cosmetics", (Chap. XL), Cosmetics—Science & Technology, John Wiley & Sons, New York, 2nd Ed., vol. 3, pp. 423-425.

*Primary Examiner*—P. E. Willis, Jr.
*Attorney, Agent, or Firm*—Kinney and Schenk

[57] ABSTRACT

It has long been the practice to incorporate bactericides, fungicides and virucides in detergent compositions. But in such detergent modifications if the antimicrobial is washed off as the hands or other surfaces are rinsed, the effectiveness of the detergent is greatly reduced. The composition should be absorbed onto the skin or other surface being washed, leaving a film which resists removal by running water. This is termed substantivity. Cinnamon oils and similar antimicrobial cinnamic compounds have been in soaps but they rinse off. A cinnamic compound-containing antimicrobial surfactant is provided herein which is rendered substantive to the surface being washed.

7 Claims, No Drawings

ANTIFUNGAL-ANTIBACTERIAL DETERGENTS CONTAINING CINNAMIC COMPOUNDS

BACKGROUND OF THE INVENTION

This invention relates to antiseptic detergents, particularly to detergents which are both antifungal and antibacterial.

Soap per se is only mildly antiseptic. A bar of nonmedicated soap will sterilize itself quickly after it has been used, but it is relatively ineffective in disinfecting the skin. Hence, soaps and synthetic detergents are of little value for surgical uses, bottle washing and the like. It has long been the practice therefore, to incorporate bactericides, fungicides and virucides in the detergent compositions. Such detergent modifications are, however, subject to two limitations. There is a surface activity factor and a toxicity factor when the detergent is to be used on the skin or as a cleaning agent in food and beverage plants.

The detergency power resulting from surface activity obviously affects the antimicrobial action of the detergent. If the antimicrobial is washed off as the hands are rinsed the effectiveness of the soap is greatly reduced. The compositions should be absorbed onto the skin or other surface being washed leaving a film which resists removal by running water.

Hexachlorophene has been frequently incorporated in medicated soaps. However it has been shown that systemic absorption of hexachlorophene results in severe lesions of the central nervous system. Other recent toxicity evidence, and the wide spectrum of microorganisms requiring antiseptic preparations, indicate a continuing need for additional antimicrobial soaps. This invention provides such soaps or detergents.

SUMMARY OF THE INVENTION

Cinnamon oils and similar cinnamic compounds have been used in soaps. However, unlike hexachlorophene which is substantive to the skin and therefore effective over a long period of time, the cinnamon compounds are washed off with rinse water. Hence their use in detergents has been limited to soap perfumery and detergent stabilization. See Vol I, *Perfumes, Cosmetics and Soaps*, W. A. Poucher, Revised by G. M. Howard (7th Ed, 1974). Cinnamon compounds are also utilized as preservatives in cosmetics (*Disinfection Sterilization & Preservation*, Seymour S. Block (2nd Ed, 1977), Chapter 39, p 779. This invention provides detergent compositions which fully utilize the antifungal and antibacterial activities of such cinnamon compounds as cinnamon oil, cinnamic aldehyde, hydrocinnamaldehyde and cinnamic acid. An antimicrobial surfactant is provided herein in the form of a detergent rendered both antifungal and antimicrobial. These new detergent compositions make possible the disinfecting of hands by scrubbing the hands with such surfactants. They will also be used in disinfecting kitchens and hospital rooms.

DETAILED DESCRIPTION OF THE INVENTION

Resident microbials which colonize on wall surfaces and on the skin and transient microorganisms which are present as contaminants or, depending on the environment, as pathogens are all potentially infectious. Resident microorganisms form the stable bacterial population on floors, walls and skin. They live and multiply there. They are firmly attached and washing removes them only slowly. Such resident bacteria are composed largely of staphylococci of little or no pathogenicity. Nevertheless, some pathogenic bacteria are almost always present.

Transient bacterial flora can be removed to a large extent by scrubbing with soap. Ultimately, nevertheless, as in the case of resident flora, the removal of bacteria requires an antimicrobial soap.

It is generally accepted that there is no relationship between disinfection and the physiochemical properties of the disinfectants. Of importance are the bacterial properties. Nonionics, for instance, have no influence on germicidal activity.

Cinnamon compounds have been found to possess the unique property of being both fungicial and bacteriacidal. They have the additional advantage of being nontoxic to human beings. For example, these edible cinnamon compounds are very effective against *Staphlococcus aureus* H, *Escherichia coli*, and *Bacillus subtilis*. The effects on growth of these bacteria of cinnamaldehyde, cinnamon oil, and hydrocinnamaldehyde (H in the table) are shown in Tables I and II.

TABLE I

Nutrient broth culture tubes inoculated with 0.1 cc of a 1:10 dilution (D-acetone): (cinnamaldehyde-acetone):

| | |
|---|---|
| *Bacillus subtilis* | cloudy, growth suspension in media |
| *Shigella dysenteriae* (Shiga) | clear, no growth |
| *Escherichia coli* | clear, no growth |
| *Myoobacterium tuberculosis* | clear, no growth |
| *Klebsiella pneumoniae* | clear, no growth |
| *Staphylococcus aureus* H | clear, no growth |
| (pH of all the cultures weakly acid) | |

TABLE II

Filter paper discs were saturated with 0.1 cc amounts of each chemical and placed in the center of the seeded plates.

| | 18-24 hrs. Zone of complete inhibition in mm. | 48 hrs. Zone of complete inhibition in mm. |
|---|---|---|
| Cinnamon oil | | |
| *B. subtilis* | 41 | 41 |
| *Staph. aureus* H | 40 | 40 |
| *E. coli* | 39 | 39 |
| Cinnamaldehyde | | |
| *B. subtilis* | 40 | 40 |
| *Staph. aureus* H | 50 | 50 |
| *E. coli* | 40 | 40 |

Using acetone and ether as diluents hydrocinnamaldehyde gave the following results on *B. subtilis*:

TABLE III

Acetone and ether controls (0.1 cc) and dilutions 800x, 1600x, 3200x, 6400x, 12800x were tested by the disc method on *Staph. aureus* H, *E. coli*, and *B. subtilis*. Neither the acetone nor the ether alone showed any positive results. Lower dilutions on *B. subtilis* gave the following:

Hydrocinnamaldehyde in acetone
 10x - clear zone of 51 mm diameter
 100x - clear zone of 25 mm diameter
 200x - more or less imperfect circular area of approx. 25 mm. Zones showed great reduction in number of organisms but no complete clearing.
 400x - an irregular circular zone of approx. 20 mm.

Hydrocinnamaldehyde in ether
 10x - clear zone of 50 mm diameter
 100x - clear zone of 15 mm diameter. Edge beyond this showed partial reduction.
 200x - no visible zone of inhibition

TABLE III-continued

Acetone and ether controls (0.1 cc) and dilutions 800x, 1600x, 3200x, 6400x, 12800x were tested by the disc method on *Staph. aureus* H, *E. coli*, and *B. subtilis*. Neither the acetone nor the ether alone showed any positive results. Lower dilutions on *B. subtilis* gave the following:

400x - no visible zone of inhibition.

As shown in our copending application the cinnamon compositions contemplated herein have also been found to be especially useful against the five common fungi. As an example, the effectiveness of these cinnamon compounds in a lanolin-petrolatum base with *Trichophyton mentagrophytes* is illustrated. The results in Table IV reflect tests after five days incubation of maltose beef serum plates.

TABLE IV

| Cinnamaldehyde | 1.5% | Entire plate clear. |
|---|---|---|
| lanolin | 5.3% by weight | |
| petrolatum | 90% by weight | |
| Hydrocinnamaldehyde | 1.5% | Entire plate clear but |
| lanolin | 5.3% by weight | for three colonies of |
| petrolatum | 90% by weight | contaminant. |
| Cinnamon oil | 1.5% | Entire plate clear but |
| lanolin | 5.3% by weight | for four contaminating |
| petrolatum | 90% by weight | colonies. |

As noted, despite their antibacterial-antifungal action, cinnamon compounds have been incorporated in soaps only for their odor and stabilization properties. We have now found how to utilize their biological action. If the soap includes compounds affording substantivity the soap is an effective antimicrobial detergent. Thus, unless the soap is compounded properly, the bacteriostat will be washed off during the rinse and thus rendered useless. This is of particular concern in surgical scrubs and in bottle washing disinfection. Indeed, the requirement eliminates a significant number of antimicrobials.

In accordance with the practice of this invention, cinnamon compounds are incorporated in soaps in such a way that they remain on the skin surface after rinsing. The detergents are made substantive. The soaps are superfatted, or an emollient is incorporated in the detergent composition. By superfatting we mean that the soap contains free fatty acids. Desirably the soap is so formulated that it has a final free fatty acid content of 1 to 5 percent by weight. The cinnamon compound is included in an amount of 0.05 to 0.3 weight percent. Examples of both types will now be given.

EXAMPLE A

In the conventional mamner a soap is compounded having the following formulation, parts being by weight:

| Formula | Parts |
|---|---|
| Coconut fatty acid | 45.0 |
| Tall oil fatty acid | 30.0 |
| Palmitic acid | 12.0 |
| Caustic potash 45% | 20.0 |
| Caustic soda 50% | 10.0 |
| Water | 156.0 |
| Propylene glycol | 18.0 |
| Water | 60.5 |
| Lonzet 143-S (isopropyl palmitate) | 6.0 |
| Tall oil fatty acid | 7.5 |
| Versenol 120 (Trisodium salt of N—hydroxyethylene-diaminetriacetic acid) | 1.5 |

| Formula | Parts |
|---|---|
| Cinnamon Oil | 0.5 |

This soap has a final free fatty acid content of 2 percent. This soap is excellent when used for the treatment of athlete's foot. If one washes with this soap and then rinses and dries, one can feel the film on the skin, as well as smell the cinnamon oil. The water beads up when added to the washed surface. It has also been found useful on locker room floors.

Any of the various soap or detergent formulations can be used in the medicated soaps of this invention so long as the free fatty acid content is in the 1 to 5 weight percent range. Examples are detergent compositions containing coconut fatty acid, tallow fatty acid, stearic acid, and oleic acid soaps, all of which are anionic. Also included are fatty acid ester soaps containing free fatty acids or emollients, for example, glyceryl monostearate, hexadecyl stearate, diethyleneglycol dioleate and the like, as well as sodium and potassium salts of fatty acids containing free fatty acids.

It makes little difference whether the detergent used is a bar soap, liquid soap, or a tincture of soap. If the water is very hard a synthetic detergent will be preferable. Synthetic detergents are particularly desirable for use in washing walls, floors and bottles. Soaps are preferred in surgical scrubs since some people find synthetic detergents harsh, and even irritating to the skin.

In the case of those detergent compositions which do not lend themselves to the inclusion of free fatty acids, an emollient can be employed in the composition. Examples are isopropyl myristate, isopropyl palmitate, isopropyl stearate, hexadecyl stearate, dihexadecyl adipate, and butyl stearate. When the detergent is rendered substantive by the inclusion of an emollient, the quantity of emollient will be from 5 to 45 weight percent (Cationic emollients may also be used).

As an example of a composition containing an emollient, the following is given, which, of course, contains 0.5 parts cinnamon oil as in Example A.

EXAMPLE B

| FORMULA | PARTS |
|---|---|
| Coconut Oil Fatty Acid | 45 |
| Refined Tall Oil Fatty Acid | 30 |
| Palmitic Acid | 12 |
| Caustic Potash (45%) | 20 |
| Caustic Soda (50%) | 10 |
| Water | 156 |
| Propylene Glycol | 18 |
| Water | 135 |
| Isopropyl Myristate | 6 |
| Refined Tall Oil Fatty Acid | 7.5 |
| Versenol | 1.5 |

Results in hand and bottle washing using this soap were similar to those when the composition of Example A was used.

The detergent compositions of this invention thus are excellent surfactant disinfectants for use in presurgical hand washing, medical instrument disinfection, wall and floor disinfection in hospitals and food plants, and disinfective cleaning in dairies, breweries, and soft drink bottling plants. Whereas wettability, detergency, and penetration power assist in antimicrobial effectiveness the cinnamon compounds can be incorporated in any detergent which can be rendered substantive either by increasing its fatty acid content, or by the incorporation of an emollient in the detergent formulation. It will be obvious too that such additives as perfumes, colorants, and the like can be included in the compositions. Such variations are deemed to be within the scope of this invention.

What is claimed is:

1. An antimicrobial surfactant in the form of a fatty acid soap rendered antifungal and antibacterial by the incorporation therein of an effective amount of a cinnamon compound selected from the group consisting of cinnamic aldehyde, cinnamon oil, hydrocinnamaldehyde, and cinnamic acid, and rendered substantive by the incorporation therein of 1 to 5 percent by weight of a free fatty acid or of 5 to 45 weight percent of an emollient.

2. The surfactant of claim 1 wherein the cinnamon compound is cinnamon oil and the free fatty acid coconut fatty acid.

3. The surfactant of claim 1 wherein the detergent is a bar soap.

4. The surfactant of claim 1 wherein the detergent is a liquid.

5. A process for disinfecting hands which comprises scrubbing the hands with the surfactant of claim 1.

6. A process for washing reuseable beverage bottles comprising washing the bottles using the surfactant of claim 1.

7. A process for cleaning kitchens and hospital rooms comprising scrubbing the floors and walls of such rooms with the surfactant of claim 1.

* * * * *